(12) United States Patent
Zimmeck et al.

(10) Patent No.: US 9,101,592 B2
(45) Date of Patent: Aug. 11, 2015

(54) STABILIZED GRANULES CONTAINING GLYCERYL TRINITRATE

(71) Applicant: G. Pohl-Boskamp GmbH & Co. KG, Hohenlockstedt (DE)

(72) Inventors: Thomas Zimmeck, Hohenlockstedt (DE); Henning Ueck, Bekmunde (DE); Julia Gehricke, Kiel (DE)

(73) Assignee: G. POHL-BOSKAMP GMBH & CO. KG, Hohenlockstedt (DE)

( * ) Notice: Subject to any disclaimer, the term of this patent is extended or adjusted under 35 U.S.C. 154(b) by 16 days.

(21) Appl. No.: 14/473,415

(22) Filed: Aug. 29, 2014

(65) Prior Publication Data

US 2014/0370109 A1    Dec. 18, 2014

Related U.S. Application Data

(63) Continuation of application No. 14/001,018, filed as application No. PCT/EP2012/000803 on Feb. 24, 2012.

(30) Foreign Application Priority Data

Feb. 25, 2011    (DE) .......................... 10 2011 012 491

(51) Int. Cl.
| | |
|---|---|
| A61K 31/21 | (2006.01) |
| A61K 9/00 | (2006.01) |
| B65D 85/00 | (2006.01) |
| A61K 47/14 | (2006.01) |
| A61K 9/14 | (2006.01) |
| A61K 9/16 | (2006.01) |
| A61J 1/03 | (2006.01) |

(52) U.S. Cl.
CPC ................. *A61K 31/21* (2013.01); *A61K 9/006* (2013.01); *A61K 9/0056* (2013.01); *A61K 9/141* (2013.01); *A61K 47/14* (2013.01); *B65D 85/00* (2013.01); *A61J 1/035* (2013.01); *A61K 9/1623* (2013.01)

(58) Field of Classification Search
CPC ....... A61K 31/21; A61K 47/14; A61K 9/141; A61K 9/0056; A61K 9/006; A61K 9/1623
See application file for complete search history.

(56) References Cited

U.S. PATENT DOCUMENTS

| | | | |
|---|---|---|---|
| 3,155,574 | A | 11/1964 | Silson et al. |
| 4,323,577 | A | 4/1982 | Ohkuma et al. |
| 4,542,013 | A | 9/1985 | Keith |
| 4,919,919 | A | 4/1990 | Aouda et al. |
| 5,186,925 | A | 2/1993 | Cholcha |
| 5,370,862 | A | 12/1994 | Klokkers-Bethke et al. |
| 5,698,589 | A | 12/1997 | Allen |
| 5,744,124 | A | 4/1998 | Klokkers-Bethke et al. |
| 8,147,872 | B2 | 4/2012 | Crew et al. |
| 2003/0095925 | A1 | 5/2003 | Dugger, III |
| 2004/0228883 | A1 | 11/2004 | Karl |
| 2005/0192210 | A1 | 9/2005 | Rothbard et al. |
| 2007/0053966 | A1 | 3/2007 | Ang et al. |
| 2007/0059346 | A1 | 3/2007 | Maibach |
| 2010/0016446 | A1 | 1/2010 | Gonda et al. |

FOREIGN PATENT DOCUMENTS

| | | |
|---|---|---|
| CA | 2718345 A1 | 9/2009 |
| DE | 3246081 A1 | 6/1984 |
| DE | 4038203 A1 | 6/1992 |
| DE | 202008007318 U1 | 9/2008 |
| DE | 102008005484 A1 | 7/2009 |
| EP | 0448961 A2 | 10/1991 |
| EP | 0461505 A1 | 12/1991 |
| EP | 0471161 A1 | 2/1992 |
| EP | 1004294 A1 | 5/2000 |
| GB | 1205019 A | 9/1970 |
| WO | 82/00005 A1 | 1/1982 |
| WO | 88/05306 A1 | 7/1988 |
| WO | 96/27372 A1 | 9/1996 |
| WO | 97/38687 A1 | 10/1997 |
| WO | 99/17766 A1 | 4/1999 |
| WO | 99/38472 A2 | 8/1999 |
| WO | 01/43735 A1 | 6/2001 |
| WO | 01/68062 A2 | 9/2001 |
| WO | 03/066472 A1 | 8/2003 |
| WO | 2004064779 A2 | 8/2004 |
| WO | 2005/004989 A1 | 1/2005 |
| WO | 2007/123955 A2 | 11/2007 |
| WO | 2009/092358 A1 | 7/2009 |
| WO | 2011/002606 A1 | 1/2011 |

OTHER PUBLICATIONS

Molecularinfo.com reference [Retrieved on Dec. 1, 2010 from the Internet: <URL: http://www.molecularinfo.com/MTM/D/D3/D3-r/D3-4-60.html], 1 pg.
Nitrolingual Pumpspray product insert (nitroglycerin lingual spray), G. Pohl-Boskamp GmbH & Co. KG, Oct. 2008, 4 pgs.
Nitrolingual Pumpspray package labelling (nitroglycerin lingual spray), G. Pohl Boskamp GmbH & Co. KG, Nov. 2008, 1 pg.
Nitrolingual Pumpspray bottle labelling (nitroglycerin lingual spray), G. Pohl-Boskamp GmbH & Co. KG, May 2006, 2 pgs.
Scheife et al., Journal of Pharmaceutical Sciences, vol. 71, Issue 1, Abstract, 1982, 1 pg.
Schranz et al., (1981), "Hemorrhagic pulmonary edema and cardiac failure following isolated head injury. Treatment with dobutamine and nitroglycerin," Monatsschr Kinderheilkd, 129 (4): 248-250. Abstract.

(Continued)

*Primary Examiner* — Sreeni Padmanabhan
*Assistant Examiner* — Jody Karol
(74) *Attorney, Agent, or Firm* — K&L Gates LLP

(57) ABSTRACT

Solid pharmaceutical preparation with the active substance glyceryl trinitrate for oromucosal or oral administration characterized in that it contains between 0.05 and 2 weight % glyceryl trinitrate, at least one carrier material, and at least one substance that reduces the volatility of the GTN, whereby this substance is a non-volatile ester stabilizer.

29 Claims, No Drawings

(56) References Cited

OTHER PUBLICATIONS

Kuroda et al., (1997), "Changes in cerebral blood flow accompanied with reduction of blood pressure treatment in patients with hypertensive intracerebral hemorrhages," Neurol Res., 19(2): 169-73. Abstract.
International Search Report for International Application No. PCT/EP2011/003890, Date of Mailing Nov. 11, 2011.
Written Opinion for International Application No. PCT/EP2011/003890, Date of Mailing Nov. 11, 2011.
Fernandes et al., (2004), "Involvement of guanylate cyclase and potassium channels on the delayed phase of mouse carrageenan-induced paw edema," European Journal of Pharmacology, Elsevier Science, NL, vol. 501, No. 1-3, pp. 209-214.
Bel Trame et al., (1998) "Nitrate therapy is an alternative to furosemidel morphine therapy in the management of acute cardiogenic pulmonary edema," Journal of Cardiac Failure, vol. 4, No. 4, pp. 271-279.
International Search Report for International Application No. PCT/EP2009/001772, Date of Mailing Jun. 16, 2009.
Written Opinion for International Application No. PCT/EP2009/001772, Date of Mailing Jun. 16, 2009.
International Search Report for International Application No. PCT/EP2012/000803, Date of Mailing Jun. 25, 2012.
Written Opinion for International Application No. PCT/EP2012/000803, Date of Mailing Jun. 25, 2012.
M. J. Pikal et al: "Vapor pressure of nitroglycerin in sublingual molded tablets: Implications for stability", Journal of Pharmaceutical Sciences, 1976, vol. 65, No. 9, pp. 1278-1284.
M. J. Pikal et al: "Polymer sorption of nitroglycerin and stability of molded nitroglycerin tablets in unit-dose packaging", Journal of Pharmaceutical Sciences, 1977, vol. 66, No. 9, pp. 1293-1297.
M. J. Pikal et al: "Effect of nitroglycerin-soluble additives on the stability of molded nitroglycerin tablets", Journal of Pharmaceutical Sciences, 1984, vol. 73, No. 11, pp. 1608-1612.
"Glyceryl Monostearate", In: R C Rowe. P J Sheskey. S C Owen: "Handbook of Pharmaceutical Excipients, 5th Edition", 2005, Pharmaceutical Press, London.
International Search Report for International Application No. PCT/EP2012/000802, Date of Mailing Jun. 6, 2012.
Written Opinion for International Application No. PCT/EP2012/000802, Date of Mailing Jun. 6, 2012.
"Barex Resins", INEOS Barex, USA, 2006, Retrieved from the Internet: URL:http://www.ineosbarex.com/files/upload/Ineos%20Barex%20Brochure.pdf, retrieved on May 15, 2012, the whole document.
Database Caplus [Online], Chemical Abstracts Service, Columbus, Ohio, US, 2004, Chen, Baoxi et al: "Effect of acrylonitrile-butadiene rubber on nitroglycerin migration from propellant to EPDM inhibitor", retrieved from STN, Database accession No. 2004:826842, abstract.
Daniel Banes: "Deterioration of nitroglycerin tablets", Journal of Pharmaceutical Sciences, vol. 57, No. 5, 1968, pp. 893-894.
European Search Report for EP12004187, Date of completion of search Sep. 28, 2012.
Cui X, et al., "Role of endothelial nitric oxide synthetase in arteriogenesis after stroke in mice", Neuroscience, New York, NY, US, vol. 159, No. 2, 2009, pp. 744-750.
Dinesh Kumar, et al., "Chronic sodium nitrite therapy augments ischemia-induced angiogenesis and arteriogenesis", Proceedings of the National Academy of Sciences, National Academy of Sciences, US, vol. 105, No. 21, 2008, pp. 7540-7545.
Hopkins et al., "Controlled delivery of vascular endothelial growth factor promotes neovascularization and maintains limb function in a rabbit model of ischemia", Journal of Vascular Surgery, C.V. Mosby CO., St Louis, MO, US, vol. 27, No. 5, 1998, pp. 886-895.
Persson et al., "Therapeutic arterigenesis in peripheral arterial disease: Combining Intervention and Passive Training", Vasa Journal for Vascular Diseases, vol. 40, No. 3, 2011, pp. 177-187.

STABILIZED GRANULES CONTAINING GLYCERYL TRINITRATE

REFERENCE TO RELATED APPLICATIONS

This is a continuation of U.S. application Ser. No. 14/001, 018, filed Aug. 22, 2013, which is the national phase of PCT/EP2012/000803, filed Feb. 24, 2012, which claims priority to and the benefit of DE 10 2011 012 491.8, filed Feb. 25, 2011, the entire contents of each of which are incorporated by reference herein.

FIELD OF INVENTION

The present invention relates to solid pharmaceutical preparations of volatile or unstable active substances. In particular, the present invention relates to solid pharmaceutical preparations for oral or oromucosal administration containing the active substance glyceryl trinitrate (nitroglycerin, referred to below in abbreviated form as GTN), which preparations are unexpectedly and surprisingly stabilized by addition of a stabilizer comprising a non-volatile ester.

BACKGROUND

GTN is an active substance which is used in the treatment of attacks of angina pectoris, among other uses, whereby it is especially used in emergency situations, in which the pharmaceutical form must enable a rapid onset of action. Within this framework sublingual administration has proven very effective with rapid uptake of the active substance and quick relief of symptoms. In addition to sublingual sprays, solutions for infusion or chewable capsules, tablets for oromucosal, i.e. sublingual or buccal administration are used as pharmaceutical forms to enable rapid onset of action.

Sprays for sublingual administration, which are used to spray the active substance-containing dose underneath the tongue, provide for a direct and rapid application of the dissolved active substance over the highly resorbent oral mucosa. However, affected patients are required to carry a relatively voluminous spray bottle around with them at all times in order to ensure immediate access to the medicinal product in emergencies and enable a rapid administration of the GTN. Alternatively, chewable capsules containing the active substance as an oily solution can be carried around as individual doses in blisters. However, a portion of the active ingredient, which is released by tearing open the capsules with the teeth, never reaches the sublingual area, its absorption is delayed or it is lost through swallowing. Sublingual tablets represent a further alternative to spray solutions and chewable capsules because they can be placed directly under the tongue to rapidly release the active substance. However, these, too, have many disadvantages which are well known.

GTN is not a stable substance. It is explosive as a pure substance and is used as an explosive in the form of dynamite. In addition, GTN is volatile even when prepared as a solid commercially available medicinal product. Phlegmatized solutions with ethanol, propylene glycol or medium chain triglycerides, for example, are less reactive and permit the safe preparation of GTN concentrates in liquid form. As a triple ester, GTN is readily hydrolyzed both in the acidic and alkaline pH range. Degradation reactions form 1,3- or 1,2-glyceryl dinitrate (GDN) and 1- or 2-glyceryl mononitrate (GMN), which limits the storage stability and shelf life of GTN formulations.

Up to now commercially available GTN tablets have been filled in glass bottles, which must be handled with a certain level of caution when carried around by patients. In addition, the removal of a single tablet can be difficult in an emergency situation, due to the small size of the tablets, among other reasons. Thus, there is a long felt unmet need for alternative forms of GTN-containing solid compounds, which are easy for patients to carry around in single-dose form, e.g. in a wallet or jacket pocket, and which simultaneously ensure sufficient stability, simple administration, and rapid onset of action.

So-called stick packs represent an alternative pharmaceutical configuration for individual doses. They can be manufactured to contain the medicinal product as free-flowing granules or powder and enable both comfortable transport of the medicinal product as well as simple and easy dosing, which is especially significant in emergency situations. However, GTN-containing powders or granules—with their substantially larger total surface area as compared with tablets—represent an even greater challenge with respect to stabilization of the composition in any type of packaging configuration including stick packs. In the case of GTN, the highest possible storage stability is especially critical to enable the patient to carry around a single dose such as but not limited to a stick pack; carrying it around in the breast pocket of a shirt, for example, can subject it to significant temperature increases and associated stress conditions, which may violate the recommended storage conditions for conventional GTN compounds.

Thus, one object of the present invention is to provide a highly stable, solid pharmaceutical preparation containing GTN, which is suitable for oromucosal administration and can be used in the production of a pharmaceutical form such as a powder, granule or tablet, which patients can carry around comfortably in an easy-to-use, unbreakable single-dose configuration such as but not limited to single doses in a stick pack. Another object of the present invention is to provide a method of production to ensure safe and reliable manufacturing on an industrial scale of a highly stabilized GTN-containing preparation and consumer medicine.

SUMMARY OF INVENTION

The present invention exploits the surprising finding that highly stable, non-liquid preparations of GTN can be manufactured using a novel process wherein GTN is combined with non-volatile carboxylic acid esters. Those esters which are suitable for this purpose are those with a melting point of 60° C. or less and which can be liquid or assume a pasty or semi-solid consistency at ambient temperatures ranging from about 15° C. to about 25° C. As described herein, it has now been discovered that a highly stabilized, non-liquid preparation of GTN results when GTN, phlegmatized in a suitable diluent to form a GTN concentrate, is then contacted with a suitable carrier material resulting in a GTN-containing slurry which is then (or contemporaneously) admixed with a suitable stabilizer in accordance with the teachings provided herein. The resulting GTN-containing absorbate is highly stable. The resulting absorbate can be in the form of a powder or granules. The absorbate can also be pressed to form a tablet type of composition. Without wishing to be bound by theory, the stabilizer entraps the GTN on and/or within the carrier material thereby preventing volatilization or escape of GTN from the non-liquid absorbate. Hence the invention results in highly prolonged shelf life and improved stability as compared with conventional GTN preparations, including GTN in a diluent customarily used for phlegmatization purposes.

The present invention is a significant advancement in the preparation and clinical availability of stabilized medicines with a prolonged shelf life whose active ingredient is, by its nature, volatile and unstable such as but not limited to GTN. The present invention has broad-reaching implications for medicinal chemistry and formularies heretofore unavailable.

In one aspect, the present invention provides a solid pharmaceutical preparation with the active substance glyceryl trinitrate for oromucosal or oral administration characterized in that it contains between 0.05 and 2 weight % glyceryl trinitrate (GTN), at least one diluent, one carrier material, and at least one substance that reduces the volatility of GTN, whereby this substance is a non-volatile ester stabilizer whose melting point is not higher than 60° C. Certain preferred preparations contain between 0.1 and 1 weight % glyceryl trinitrate. The non-volatile ester stabilizer can be solid or semi-solid at a temperature of 20° C. in certain preferred embodiments while the non-volatile ester stabilizer can be liquid in others. In preferred embodiments, the non-volatile ester stabilizer is selected from the group consisting of: mono- and diglycerides, polyethoxylated glycerides, esters of lactic acid, D-alpha tocopheryl polyethylene glycol 1000 succinate and solid triglycerides, and mixtures of any one of these substances. The non-volatile ester stabilizer can be used at a concentration of 0.2 to 10 weight %, based on the total weight of the preparation. According to the present invention, the GTN, diluent and stabilizer form a homogeneous preparation in some embodiments. In currently preferred embodiments, the mass ratio of the non-volatile ester stabilizer to GTN is between 2 and 40; and the mass ratio of the diluent to non-volatile ester stabilizer is between 1 and 9.5. In some preferred embodiments, the carrier material is selected from the group consisting of: magnesium aluminometasilicate, dibasic calcium phosphate, isomalt and mixtures of any one of the foregoing.

According to the present invention, the above-described solid pharmaceutical preparation can further include at least one excipient suitable for sublingual administration, which is selected from the group consisting of: water-soluble mono-, di-, and polysaccharides, as well as their alcohols. In currently preferred embodiments, the excipient suitable for sublingual administration is selected from the group consisting of: fructose, glucose, isomalt, lactose, maltose, maltitol, mannitol, sorbitol, sucrose, trehalose, and xylitol and mixtures of any one of the foregoing. In particularly preferred embodiments, the excipient suitable for sublingual administration is xylitol and/or isomalt at concentrations of between 20 and 95 weight %. In even more preferred embodiments, the excipient suitable for sublingual administration is isomalt, which is contained at concentrations of between 70 and 95 weight %, based on the total weight of the preparation.

In yet other embodiments of the solid pharmaceutical preparation, the preparation further comprises at least 0.01 to 3.0 weight % of a flavoring agent.

One particularly preferred embodiment of the solid pharmaceutical preparation for oromucosal or oral administration contains an absorbate comprising between 0.05 and 2 weight % GTN and a non-volatile ester stabilizer on a carrier material.

According to the teachings of the present invention, any of the foregoing solid pharmaceutical preparation can be in the form of a free-flowing powder or free-flowing granules. They can be packaged as a single dose in the form of a stick pack or sachet.

In another aspect, the present invention provides a process for the manufacture of a pharmaceutical preparation with the active substance glyceryl trinitrate for oromucosal or oral administration characterized in that it contains between 0.05 and 2 weight % glyceryl trinitrate (GTN), the process comprising the steps of: a) preparing a mixture comprising at least one carrier material selected from the group consisting of: magnesium aluminometasilicate, dibasic calcium phosphate, fructose, glucose, isomalt, lactose, maltose, maltitol, mannitol, sorbitol, sucrose, trehalose, xylitol and mixtures of any one of the foregoing; b) preparing a GTN solution comprising at least one non-volatile ester stabilizer whose melting point is not higher than 60° C.; c) adding in a step-wise fashion the GTN solution to the carrier material; and d) mixing until the active substance has been homogeneously distributed, optionally followed by a drying step.

In yet another aspect, the present invention provides a process for the manufacture of a solid pharmaceutical preparation with the active substance GTN for oromucosal or oral administration characterized in that it contains between 0.05 and 2 weight % GTN, the process comprising the steps of: a) preparing a GTN solution comprising phlegmatized GTN and at least one non-volatile ester stabilizer; b) adding in a stepwise manner the GTN solution formed in step a) to a carrier material; c) optionally adding further excipients; d) mixing until the active substance has been homogeneously distributed, optionally followed by a drying step.

In a further aspect, the present invention provides a process for the manufacture of a solid pharmaceutical preparation with the active substance GTN for oromucosal or oral administration characterized in that it contains between 0.05 and 2 weight % GTN, the process comprising the steps of: a) providing GTN admixed with at least one non-volatile ester stabilizer; b) adding in a stepwise manner the GTN—stabilizer admixture of step a) to a carrier material; c) optionally adding further excipients; and d) mixing until the active substance has been homogeneously distributed, optionally followed by a drying step.

DETAILED DESCRIPTION OF INVENTION

For purposes of clarification, and in no manner intended to be limiting, the following definition of terms used herein is provided:

Diluent is a substance which permits phlegmatization of a volatile substance such as GTN and permits safe preparation of a liquid concentrate. As also described elsewhere herein, suitable diluents include, for example (but not limited to), medium chain triglycerides (MCT) (e.g., $C_{6-12}$), propylene glycol and ethanol. For example, when reference herein is made to a GTN concentrate, it is GTN phlegmatized in a suitable diluent such as, for example, MCT.

Stabilizer is a substance which increases the stability of a volatile substance such as GTN beyond that exhibited by the substance in a mere diluent. As also described elsewhere herein, suitable stabilizers include but are not limited to non-volatile carboxylic acid esters. Generally speaking and as described elsewhere herein, suitable stabilizers can be selected from a group of carboxylic acid esters with similar polarity as GTN and which may be liquid, solid or semi-solid at ambient temperatures but liquefy at about 60° C. For purposes of the present invention, MCT such as, for example, medium chain triglycerides according to the European Pharmacopoeia are not contemplated as a stabilizer within the teachings of the present invention.

Carrier material is a non-liquid substance which renders a composition according to the present invention as a powder or a granule. As also described elsewhere herein, suitable carrier materials include but are not limited to water soluble carbohydrates and their respective alcohols such as, but not limited to, isomalt which has a porous structure and inorganic compounds with porous structures such as, but not limited to, anhydrous dibasic calcium phosphate and magnesium aluminometasilicate, or mixtures of any one of the foregoing.

Absorbate as used herein means a composition comprising an admixture of at least an active ingredient such as GTN in a phlegmatized form with at least one carrier material and a stabilizer. For purposes of the present invention, the mass ratio between diluent and stabilizer in one currently preferred embodiment is 19:5; in certain other preferred embodiments, the ratio is 19:10. In yet other preferred embodiments the diluent:stabilizer mass ratio is 19:2, 19:3, 19:4, 19:6, 19:7, 19:8, 19:9, 19:12, 19:15, and 1:1.

The teachings of the present invention have resulted in the surprising and unexpected finding that the free-flowing absorbate with its at least 10-fold greater surface area as compared with a conventional compressed tabletized form of GTN can minimize or prevent volatilization and/or evaporation of GTN, even though the GTN in theory has a greater opportunity to escape due to the absorbate's extensive surface area. One of skill in the art would not have predicted this based on the state of the art before the present invention.

As described above, the objectives of the present invention are solved by a GTN-containing pharmaceutical preparation which is stable during storage, in the form of a free-flowing powder or granules, which, in addition to at least one non-liquid carrier substance and optional additional excipients, comprises at least one stabilizer substance, which significantly reduces the volatility of GTN and is selected from the group of non-volatile esters whose melting point is not higher than 60° C. Without remaining bound by this theory, it is assumed that esters with a polarity very close to that of GTN surround the GTN molecules on the inner surface of the carrier material and prevent volatilization of the GTN. Stabilizers, which are solid, semi-solid or pasty at room temperature, are especially well suited as exemplified below. Again, without remaining bound by this theory, it is currently thought that the absorbed solutions which form the absorbate, which partially or completely solidify following preparation, are especially effective at trapping and thereby preventing the GTN from evaporating. For example, when a porous carrier is used, the GTN becomes encapsulated in the pores of the carrier as the stabilizer substance solidifies in the pores. The pharmaceutical preparation according to the invention is suitable for filling in individual packages, such as stick packs, capsules or sachets, for example. In the case of stick packs, particularly preferred materials and configurations are described in (1) International Patent Application filed on even date herewith, the entire contents of which is herein incorporated by reference and (2) German Patent Application No. DE 10 2011 012 491.8 filed on Feb. 25, 2011, to which this application and the aforementioned International Patent Application claim priority. According to DE 10 2011 012 491.8 (e.g. example 5) the preferred materials for packaging the GTN containing preparation according to the invention are composite films which contain a layer comprising a copolymer of acrylonitrile units and one or more other monomers (AN-copolymers) on the surface facing the pharmaceutical preparation. In the case of stick packs, most preferred are aluminium composite films containing a layer made of acrylonitrile-methylacrylate copolymer or impact-modified acrylonitrile-methylacrylate copolymer on the side, which is in contact with the pharmaceutical composition. The pharmaceutical preparations and methods of the present invention can also be used, however, for the eventual production of other solid pharmaceutical forms, e.g. tablets, mini-tablets or pellets.

Particularly significant advantage of one aspect of the present invention is that production of pharmaceutical preparations of volatile, unstable ingredients can be carried out without the use of volatile and flammable solvents, enabling the preparations to be manufactured without the use of energy-intensive drying steps and elaborate solvent recovery processes. However, the present invention also contemplates production of pharmaceutical preparations of volatile ingredients such as GTN phlegmatized in ethanol.

Within the framework of the tests exemplified below, upon which the invention was discovered, it was unexpectedly discovered that the volatility of GTN is significantly reduced under both standard storage conditions as well as under stress conditions through the use of a non-volatile ester stabilizer whose melting point is not higher than about 60° C. For the purposes of the invention non-volatile means that the stabilizer substance preferably has a boiling point above or at about 200° C. (measured at normal ambient pressure). The preferred maximum melting point of 60° C. results from the fact that the GTN is also heated to this temperature during the absorbate production process. Higher temperatures should be avoided due to stability issues of the GTN. A more preferred melting point is at or about 0 to 50° C., an even more preferred melting point is at or about 20 to 45° C., and a most preferred melting point is at or about 30 to 40° C. Furthermore, and very importantly, the use of the ester stabilizer described herein does not compromise the disintegration properties of the granules, the release of the active substance, or its absorption into the body. The processes of the present invention result in a clinically advantageous composition, which induces a rapid absorption of the active substance when customarily administered via the oral mucosa and a resulting rapid reduction in the symptoms of the condition in life-threatening emergencies such as an attack of angina pectoris.

As described earlier, the present invention's GTN component is provided in the form of a phlegmatized GTN concentrate; in a preferred embodiment, the diluent for such a concentrate is MCT. Due to its explosive properties, GTN intended for pharmaceutical purposes is phlegmatized by the manufacturer, which reduces the risk posed by the hazardous properties. The matrix used for phlegmatization can be in liquid and/or powder form. For example, GTN is commercially available as a 5% solution in MCT, such as Miglyol® 812, as a 5% solution in propylene glycol, as a 10% concentrate in lactose triturate or a 2.25% dilution in glucose. Miglyol® 812 is a preparation comprising a fatty acid fraction of a maximum of about 2% caproic acid ($C_{6:0}$), about 50-80% caprylic acid ($C_{8:0}$), about 20-50% capric acid ($C_{10:0}$), a maximum of about 3% lauric acid ($C_{12:0}$), and a maximum of about 1% myristic acid ($C_{14:0}$) in keeping with the art-recognized standards set by the European Pharmacopoeia. If these GTN concentrates are used directly for the preparation of the absorbate according to the invention, then the diluent used for phlegmatization is also contained in the finished product. According to the present invention, a preferred ratio of diluent:stabilizer is between about 1 and 8; more preferably between about 1.2 and 5.0, even more preferably between about 1.5 and 4.0; and most preferably between about 1.9 and 3.8. In other equally useful embodiments of the present invention, GTN can be phlegmatized in a volatile solvent such as but not limited to ethanol; in such instances, little or no diluent is present in the finished product.

The stabilized GTN-containing composition according to the invention comprises an absorbate comprising concentrations of at or about 0.2 to 10 weight % of the non-volatile ester stabilizer having a melting point not higher than or at about 60° C.; stabilizer concentrations in certain preferred embodiments include 0.5, 1.0, 1.5, 2.0, 2.5, 3.0, 4.0, 5.0, 6.0, 7.0 or 8.0 weight %. It is also contemplated to use mixtures of the stabilizing esters described. In such cases, the quantities refer to the total for these substances. The GTN concentration in the final absorbate composition is within a range of at or about 0.05 to 2 weight %; in certain preferred embodiments GTN concentrations include 0.10, 0.15, 0.20, 0.25, 0.30, 0.35, 0.40, 0.50, 0.60, 0.70, 0.80, 1.0 or 1.5 weight %. Unless otherwise stated, all weight percentages refer to the total composition. The mass ratio of stabilizer(s):GTN is within the range of at or about 2 to 40; one preferred embodiment includes a ratio of 4 to 20, while a ratio of 5, 10, and 15 is particularly preferred in other embodiments.

As earlier explained, in a preferred embodiment of the invention the non-volatile ester stabilizer whose melting point is not higher than or at about 60° C. is selected from the group of liquid, solid, semi-solid or pasty substances at room temperature. In particularly preferred embodiments of the invention, the stabilizer is chosen from a group of substances that result in a homogeneous solution when admixed with the phlegmatized GTN concentrate. Especially preferred stabilizer substances are solid or pasty at room temperature, and include but are not limited to triglycerides, diglycerides, and monoglycerides; polyethoxylated triglycerides, diglycerides, and monoglycerides; esters of lactic acid; and D-alpha tocopheryl polyethylene glycol 1000 succinate (TPGS). As proposed earlier, it is suspected that the absorbates, which partially or completely solidify following preparation, are especially effective at preventing the GTN from evaporating.

In the case of stabilizers selected from the group consisting of triglycerides, preferred triglycerides include, for example, hard fat in accordance with USP/NF, which is, e.g., commercially available as Gelucire™ 43/01 from Gattefossé (Saint-Priest Cedex, France). In the case of mono- and diglycerides include, for example, glycerol monooleate, which is, e.g., commercially available as Cithrol® GMO HP from Croda GmbH (Nettetal, Germany), glycerol monocaprylocaprate in accordance with the European Pharmacopeia (Ph. Eur.), sold for example under the commercial name Capmul™ MCM EP by Abitec (Janesville, USA), or mono- and diglycerides in accordance with USP/NF. Polyethoxylated glycerides include for example oleoyl macrogol-6-glycerides in accordance with USP/NF, which are, e.g., commercially available as Labrafil® 1944CS from Gattefossé. In other embodiments, preferred stabilizers are selected from the group consisting of esters of lactic acid including, for example, cetyl lactate and myristyl lactate, which are, e.g., commercially available as Crodamol™ CL and Crodamol™ ML resp. from Croda GmbH (Nettetal, Germany).

The absorbate composition according to the invention also contains at least one pharmaceutically suitable carrier material characterized by a large inner surface area capable of absorbing, for example, oily liquids. Preferred carrier materials of that kind include, but are not limited to, magnesium aluminometasilicate in accordance with USP/NF, one example of which is commercially available as Neusilin® US2 from Fuji Chemical Industry (Japan), anhydrous dibasic calcium phosphate in accordance with USP/NF, one example of which is commercially available as Fujicalin® from Fuji Chemical Industry (Japan), isomalt according to the European Pharmacopoeia one example of which is commercially available as Galen IQ™ from BENEO-Palatinit GmbH (Mannheim, Germany) or mixtures of any one of the foregoing types of carrier materials.

The absorbate composition according to the invention can also contain other pharmaceutically acceptable excipients which support sublingual release of the active substance and are selected (but not limited to) from among the group water-soluble mono-, di-, and polysaccharides, as well as their alcohols. This excipient is selected especially from the group including but not limited to fructose, glucose, isomalt, lactose, maltose, maltitol, mannitol, sorbitol, sucrose, trehalose, and xylitol and/or mixtures thereof. In certain preferred embodiments, these excipients are present at a total concentration of at or about 70 to 95 weight %. In the case of mixtures the concentration of each individual substance is at or about 20 to 95 weight %, whereby in certain other preferred embodiments concentrations include 25, 30, 35, 40, 45, 50, 55, 60, 65, 70, 75, 80, or 85 weight %. In certain embodiments, isomalt is especially preferred. It can serve both as a carrier material when a diluent for the active ingredient such as GTN is an oily solution and can also serve as additional bulk material.

In addition, the absorbate preparation according to the invention can contain other excipients, such as flavoring agents. Flavoring agents are used especially in the case of preparations for oral or sublingual administration in order to increase acceptance among patients. In certain preferred embodiment according to the invention, they are used at concentrations of at or about 0.01 to 3.0 weight %, whereby the especially preferred concentrations in certain other embodiments include at or about 0.1, 0.5, 1, 1.5, 2 or 2.5 weight %.

A currently preferred formula comprises:

| Contents | Quantity [g] |
| --- | --- |
| GTN (5%) in diluent MCT | 79.35 |
| Glycerol monocaprylocaprate Ph. Eur. | 19.85 |
| Anhydrous dibasic calcium phosphate | 100.80 |
| Isomalt | 1800.00 |
| Total | 2000.00 |
| GTN concentration | 0.2% |

Another currently preferred formula comprises:

| Contents | Quantity [g] |
| --- | --- |
| GTN (5%) in diluent MCT | 40.0 |
| Solid Triglycerides | 20.0 |
| Anhydrous dibasic calcium phosphate | 49.9 |
| Isomalt | 880.1 |
| Peppermint flavoring agent | 10.0 |
| Total | 1000.00 |
| GTN concentration | 0.2% |

Yet another currently preferred formula comprises:

| Contents | Quantity [g] |
| --- | --- |
| GTN (5%) in diluent MCT | 40.0 |
| Oleoyl macrogol-6-glycerides | 20.0 |
| Anhydrous dibasic calcium phosphate | 50.0 |
| Isomalt | 880.0 |
| Peppermint flavoring agent | 10.0 |
| Total | 1000.00 |
| GTN concentration | 0.2% |

And, another currently preferred formula comprises:

| Contents | Quantity [g] |
| --- | --- |
| GTN (5%) in diluent MCT | 40.0 |
| Solid Triglycerides | 10.0 |

-continued

| Contents | Quantity [g] |
| --- | --- |
| Glycerol monocaprylocaprate Ph. Eur. | 10.0 |
| Anhydrous dibasic calcium phosphate | 50.0 |
| Isomalt | 880.0 |
| Peppermint flavoring agent | 10.0 |
| Total | 1000.00 |
| GTN concentration | 0.2% |

And, yet another currently preferred formula comprises:

| Contents | Quantity [g] |
| --- | --- |
| GTN (5%) in diluent MCT | 40.0 |
| Oleoyl macrogol-6-glycerides | 10.0 |
| Triglycerides | 10.0 |
| Anhydrous dibasic calcium phosphate | 50.0 |
| Isomalt | 880.0 |
| Peppermint flavoring agent | 10.0 |
| Total | 1000.0 |
| GTN concentration | 0.2% |

And, another currently preferred formula comprises:

| Contents | Quantity [g] |
| --- | --- |
| GTN (5%) in diluent propylene glycol | 4.0 |
| Glycerol monocaprylocaprate Ph. Eur. | 1.0 |
| Anhydrous dibasic calcium phosphate | 5.0 |
| Isomalt | 89.0 |
| Peppermint flavoring agent | 1.0 |
| Total | 100.00 |
| GTN concentration | 0.2% |

And, yet another currently preferred formula comprises:

| Contents | Quantity [g] |
| --- | --- |
| GTN (5%) in diluent propylene glycol | 4.0 |
| Oleoyl macrogol-6-glycerides | 2.0 |
| Anhydrous dibasic calcium phosphate | 5.0 |
| Isomalt | 88.0 |
| Peppermint flavoring agent | 1.0 |
| Total | 100.0 |
| GTN concentration | 0.2% |

And, another currently preferred formula comprises:

| Contents | Quantity [g] |
| --- | --- |
| GTN 5% in diluent ethanol | 4.0 |
| Glycerol monooleate | 4.0 |
| Anhydrous dibasic calcium phosphate | 5.0 |
| Isomalt | 89.8 |
| Peppermint flavoring agent | 1.0 |
| Total | 103.8 |
| GTN concentration after evaporation of ethanol | 0.2% |

And, yet another currently preferred formula comprises:

| Contents | Quantity [g] |
| --- | --- |
| GTN | 0.2 |
| Oleoyl macrogol-6-glycerides | 4.0 |
| Anhydrous dibasic calcium phosphate | 5.0 |
| Isomalt | 89.8 |
| Peppermint flavoring agent | 1.0 |
| Total | 100.0 |
| GTN concentration | 0.2% |

In one preferred aspect of the invention, the production method according to the present invention comprises the mixture of a concentrate of a volatile chemical, such as for example a GTN concentrate in which GTN is solubilized in a suitable diluent with a non-volatile ester stabilizer whose melting point is not higher than about 60° C. until a homogeneous solution results. In certain embodiments, stabilizing esters not already in liquid form at room temperature are heated to a maximum temperature of about 10° C. above their melting point and then mixed with the GTN concentrate as described above at that temperature. This intermediate solution is then admixed with a carrier material which is powdered or granulated and mixed mechanically until a homogeneous, free-flowing powder or granulate absorbate is formed. For purposes of the present invention, free-flowing powder or granulate absorbate means an absorbate which does not have a wet or oily or sticky consistency or is not a liquid. In another embodiment, the GTN concentrate can first be combined with a carrier material capable of absorbing especially large quantities of oil—up to 100% of its own weight, for example—and then the other components such as the stabilizer can be added. Thus in certain embodiments in which the active substance now contained in a carrier material is mixed with the non-volatile ester stabilizer whose melting point is not higher than 60° C., it is possible to dispense entirely with the use of volatile and flammable solvents during the production process. This enables the production of a preferred embodiment of the absorbate according to the invention without energy-intensive drying steps and elaborate solvent recovery processes. Thus, one preferred embodiment of the production process of the present invention is especially suitable on an industrial scale. This is a significant advancement with industrial benefits heretofore unavailable.

However, as described earlier, other embodiments of the production process of the present invention contemplate the use of GTN concentrates comprising a volatile solvent such as ethanol. Even in the case of this particular production process, a heretofore unavailable stabilized free-flowing absorbate can still be successfully manufactured without any disadvantages or compromises in the resulting absorbate. In the case of an embodiment of the production method in which a GTN concentrate in a volatile diluent is used, the concentrate is absorbed by a solid carrier material and contemporaneously or in a second step the liquid or liquefied stabilizing ester is added. The resulting slurry is dried, for example at a temperature of 30° C. Then the other excipients are added and mixed until a homogeneous free flowing powder or granulate absorbate is formed.

In yet another embodiment of the production method of the present invention, GTN can be diluted under careful attention of the explosion risk directly in the stabilizing ester. This mixture is then absorbed by a solid carrier material. Then the other excipients are added and mixed until a homogeneous free flowing powder or granulate absorbate is formed. This process is most suitable when the stabilizer is a liquid.

In any of the proposed production methods described herein, a sieving or disaggregating step can be employed in order to ameliorate the flowing behavior of the powder mixture.

In yet another embodiment of the production method of the present invention, the method can differ from the above in that first a GTN concentrate is absorbed by a solid carrier material and second the liquid or liquefied stabilizing ester is added. Then the other excipients are added and mixed until a homogenous free flowing powder or granulate absorbate is formed. This process is especially effective if stabilizer and GTN in diluent cannot be mixed homogeneously e.g. solid triglycerides as stabilizers and GTN in diluent propylene glycol.

EXAMPLES

The following Examples illustrate the production of various formulations according to the invention without reducing the scope of the invention to these Examples.

Comparative Example 1

Commercially available GTN tablets each with a total weight of 35 mg, containing 0.4 mg GTN and lactose monohydrate, glycerol monostearate, pre-agglutinated starch, calcium stearate and colloidal silicon dioxide as excipients, were packaged individually in film stick packs and stored at 40° C./75% rel humidity for three months.

Comparative Example 2

| Contents | Quantity [g] |
| --- | --- |
| GTN in diluent lactose monohydrate 10% | 0.60 |
| Polyethylene glycol 400 | 0.36 |
| Isomalt | 16.81 |
| Xylitol | 12.01 |
| Silicon dioxide (Aeroperl ®) | 0.25 |
| Total | 30.03 |
| GTN concentration | 0.20% |

The active substance triturate was mixed well with the liquid polyethylene glycol; the other substances were added in the sequence listed above and mixed. 200-mg portions of the free-flowing powder were filled in stick packs and stored at 40° C./75% rel humidity for three months.

Example 1

| Contents | Quantity [g] |
| --- | --- |
| GTN (5%) in diluent MCT | 1.033 |
| Triethyl citrate | 1.032 |
| Isomalt | 16.513 |
| Xylitol | 6.248 |
| Silicon dioxide (Aeroperl ®) | 0.207 |
| Total | 25.033 |
| GTN concentration | 0.207% |

Triethyl citrate was mixed with GTN phlegmatized in a diluent of medium chain triglycerides (MCT). The solution was mixed well with the isomalt. Then xylitol and finally silicon dioxide were added and mixing was continued. 200-mg portions of the free-flowing powder were filled in stick packs and stored at 40° C./75% rel humidity for three months.

The GTN concentration was quantified after production and at various points during storage using HPLC analysis. The individual doses were dissolved in a suitable solvent to perform the analysis. The GTN was detected using a UV-VIS detector at a wavelength of 225 nm.

| GTN concentration following storage at 40° C./75% rel. humidity | | | | |
| --- | --- | --- | --- | --- |
| Product according to | 0 months | 2 weeks | 1 month | 3 months |
| Comp. example 1 | 0.391 mg | 0.079 mg | 0.065 mg | * |
| Comp. example 2 | 0.407 mg | n.c. | 0.305 mg | 0.245 mg |
| Example 1 | 0.415 mg | n.c. | n.c. | 0.394 mg |

* The test was terminated after one month because more than 80% of the active substance had already been lost.
n.c.—not conducted This initial comparative test proves that neither the commercially available tablet, nor a powder mixture with the substances contained in a conventional tablet, nor a preparation with polyethylene glycol is suitably stable in a stick pack. The only acceptable level of storage stability was achieved with the addition of the stabilizing ester according to the invention together with a GTN concentrate phlegmatized in MCT as a liquid.

Example 2

| Contents | Quantity [g] |
| --- | --- |
| GTN (5%) in diluent MCT | 2.00 |
| TPGS | 1.00 |
| Magnesium aluminometasilicate | 2.50 |
| Isomalt | 44.5 |
| Total | 50.00 |
| GTN concentration | 0.20% |

TPGS was melted at 50° C. and mixed with GTN concentrate in a diluent of MCT. While still warm, the mixture was blended well with the magnesium aluminometasilicate. Then isomalt was added and mixing was continued. 200-mg portions of the free-flowing powder were filled in stick packs and stored at 25° C./60% rel. humidity. The GTN concentration was quantified immediately after production and at various points during storage as disclosed under Example 1. The results are presented in the following table:

| Storage duration/temp. | 0 months | 3 months/25° C. | 6 months/25° C. |
| --- | --- | --- | --- |
| GTN concentration | 0.400 mg | 0.398 mg | 0.392 mg |

Example 3

| Contents | Quantity [g] |
| --- | --- |
| GTN (5%) in diluent MCT | 2.02 |
| Glycerol monocaprylocaprate Ph. Eur. | 0.52 |

-continued

| Contents | Quantity [g] |
|---|---|
| Magnesium aluminometasilicate | 1.50 |
| Isomalt | 45.99 |
| Total | 50.03 |
| GTN concentration | 0.20% |

The glycerol monocaprylocaprate was melted at 40° C. and mixed with a GTN concentrate in MCT diluent. While still warm, the mixture was blended well with the magnesium aluminometasilicate. Then isomalt was added and mixing was continued. 200-mg portions of the free-flowing powder were filled in stick packs and stored at 40° C./75% rel humidity and at 25° C./60% rel. humidity. The GTN concentration was quantified immediately after production and at various points during storage as disclosed under Example 1. The results are presented in the following table:

| Storage duration/temp. | 0 months | 6 months/25° C. | 6 months/40° C. |
|---|---|---|---|
| GTN concentration | 0.397 mg | 0.383 mg | 0.355 mg |

Example 4

| Contents | Quantity [g] |
|---|---|
| GTN (5%) in diluent MCT | 79.35 |
| Glycerol monocaprylocaprate Ph. Eur. | 19.85 |
| Anhydrous dibasic calcium phosphate | 100.80 |
| Isomalt | 1800.00 |
| Total | 2000.00 |
| GTN concentration | 0.2% |

The glycerol monocaprylocaprate was melted at 40° C. and mixed with a GTN concentrate in a MCT diluent. While still warm, the mixture was blended well with the anhydrous dibasic calcium phosphate. Then isomalt was added and mixing was continued. 200-mg portions of the free-flowing powder were filled in stick packs and stored at 40° C./75% rel humidity and at 25° C./60% rel. humidity. The GTN concentration was quantified immediately after production and at various points during storage as disclosed under Example 1. The results are presented in the following table:

| Storage duration | 0 months | 3 months | 6 months |
|---|---|---|---|
| GTN concentration at 40° C. | 0.380 mg | 0.380 mg | 0.383 mg |
| GTN concentration at 25° C. | 0.380 mg | 0.380 mg | 0.379 mg |

Comparative Example 3

| Contents | Quantity [g] |
|---|---|
| GTN (5%) in diluent MCT | 1.193 |
| Anhydrous dibasic calcium phosphate | 1.513 |

-continued

| Contents | Quantity [g] |
|---|---|
| Isomalt | 19.80 |
| Xylitol | 7.50 |
| Total | 30.006 |
| GTN concentration | 0.2% |

GTN concentrate in MCT diluent was blended well with the anhydrous dibasic calcium phosphate. Then isomalt and xylitol were added and mixing was continued. 200-mg portions of the free-flowing powder were filled in stick packs and stored at 40° C./75% rel humidity and at 25° C./60% rel. humidity. The GTN concentration was quantified immediately after production and at various points during storage as disclosed under Example 1. The results are presented in the following table:

| Storage duration | 0 months | 3 months |
|---|---|---|
| GTN concentration at 40° C. | 0.410 mg | 0.340 mg |
| GTN concentration at 25° C. | 0.410 mg | 0.363 mg |

A comparison between the data from Example 4 according to the invention and the non-stabilized preparation according to comparative Example 3 reveals that a clinically significant average loss of 17% and 11% occurred without stabilization after a storage period of three months at 40° C. and 25° C., respectively. A product having this degree of susceptibility to deterioration and loss of active ingredient is not suitable commercially for sale as a pharmaceutical. In sharp contrast, the content of the active substance in Example 4 remained nearly constant for six months when in the presence of a stabilizer in accordance with the present invention.

The following Examples illustrate further the benefit of stabilized formulas according to the invention. Additionally, the following Examples demonstrate the benefits of mixtures of the stabilizers as contemplated by the present invention. Importantly, the following Examples illustrate stabilization obtained at even more elevated temperatures, i.e., 50° C.:

Example 5

| Contents | Quantity [g] |
|---|---|
| GTN (5%) in diluent MCT | 43.9 |
| Glycerol monocaprylocaprate Ph. Eur. | 16.6 |
| TPGS | 16.6 |
| Magnesium aluminometasilicate | 54.9 |
| Isomalt | 957.0 |
| Peppermint flavoring agent | 11.0 |
| Total | 1100.00 |
| GTN concentration | 0.2% |

The glycerol monocaprylocaprate and TPGS were melted at 50° C. and mixed with GTN concentrate in MCT diluent. While still warm, the mixture was blended well with the magnesium aluminometasilicate. Then isomalt and peppermint flavoring agent were added and mixing was continued. 200-mg portions of the free-flowing powder were filled in stick packs and stored at 50° C. and at 40° C./75% rel. humidity. The GTN concentration was quantified immediately after production and at various points during storage as disclosed under Example 1.

Example 6

| Contents | Quantity [g] |
| --- | --- |
| GTN (5%) in diluent MCT | 40.0 |
| Solid Triglycerides | 20.0 |
| Anhydrous dibasic calcium phosphate | 49.9 |
| Isomalt | 880.1 |
| Peppermint flavoring agent | 10.0 |
| Total | 1000.00 |
| GTN concentration | 0.2% |

The solid triglycerides were melted at 50° C. and mixed with GTN concentrate in MCT diluent. While still warm, the mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity. The GTN concentration was quantified immediately after production and at various points during storage as disclosed under Example 1.

Example 7

| Contents | Quantity [g] |
| --- | --- |
| GTN (5%) in diluent MCT | 40.0 |
| Solid Triglycerides | 10.0 |
| Glycerol monocaprylocaprate Ph. Eur. | 10.0 |
| Anhydrous dibasic calcium phosphate | 50.0 |
| Isomalt | 880.0 |
| Peppermint flavoring agent | 10.0 |
| Total | 1000.00 |
| GTN concentration | 0.2% |

The solid triglycerides and glycerol monocaprylocaprate were melted at 50° C. and mixed with a GTN concentrate in MCT diluent. While still warm, the mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity. The GTN concentration was quantified immediately after production and at various points during storage as disclosed under Example 1.

Example 8

| Contents | Quantity [g] |
| --- | --- |
| GTN (5%) in diluent MCT | 40.0 |
| Oleoyl macrogol-6-glycerides | 20.0 |
| Anhydrous dibasic calcium phosphate | 50.0 |
| Isomalt | 880.0 |
| Peppermint flavoring agent | 10.0 |
| Total | 1000.00 |
| GTN concentration | 0.2% |

The oleoyl macrogol-6-glycerides were mixed with GTN in MCT. The mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity. The GTN concentration was quantified immediately after production and at various points during storage as disclosed under Example 1.

Example 9

| Contents | Quantity [g] |
| --- | --- |
| GTN (5%) in diluent MCT | 40.0 |
| Glycerol monooleate | 20.0 |
| Anhydrous dibasic calcium phosphate | 50.0 |
| Isomalt | 880.0 |
| Peppermint flavoring agent | 10.0 |
| Total | 1000.00 |
| GTN concentration | 0.2% |

The glycerol monooleate was melted at 50° C. and mixed with a GTN concentrate in MCT diluent. The mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity. The GTN concentration was quantified immediately after production and at various points during storage as disclosed under Example 1.

The results from the storage tests with the preparations from Examples 5-9 are presented in the following table:

| Storage duration at 50° C. | 0 months | 1 month | 2 months |
| --- | --- | --- | --- |
| Example 5 | 0.404 mg | 0.380 mg | 0.369 mg |
| Example 6 | 0.394 mg | 0.390 mg | 0.384 mg |
| Example 7 | 0.391 mg | 0.393 mg | 0.389 mg |
| Example 8 | 0.394 mg | 0.392 mg | 0.388 mg |
| Example 9 | 0.390 mg | 0.376 mg | 0.377 mg |

Taken together the results unambiguously show that loss of GTN is significantly reduced through the addition of a non-volatile ester stabilizer as compared with the stabilizer-free composition from comparative Examples 2 and 3.

Example 10

| Contents | Quantity [g] |
| --- | --- |
| GTN (5%) in diluent MCT | 40.0 |
| Oleoyl macrogol-6-glycerides | 10.0 |
| Triglycerides | 10.0 |
| Anhydrous dibasic calcium phosphate | 50.0 |
| Isomalt | 880.0 |
| Peppermint flavoring agent | 10.0 |
| Total | 1000.0 |
| GTN concentration | 0.2% |

Oleoyl macrogol-6-glycerides and triglycerides were mixed with GTN phlegmatized in MCT. The mixture was blended well with the anhydrous dibasic calcium phosphate.

Then isomalt was added in portions followed by the peppermint flavoring agent and mixing was continued. 200-mg portions of the free-flowing powder were filled in stick packs and stored at 50° C. and at 40° C./75% rel. humidity.

Example 11

| Contents | Quantity [g] |
| --- | --- |
| GTN (5%) in diluent MCT | 40.0 |
| Glycerol monooleate | 10.0 |
| Mono- and Diglycerides | 10.0 |
| Anhydrous dibasic calcium phosphate | 50.0 |
| Isomalt | 880.0 |
| Peppermint flavoring agent | 10.0 |
| Total | 1000.0 |
| GTN concentration | 0.2% |

Glycerol monooleate and mono- and diglycerides (type Geleol) were melted at 50° C. and mixed with a GTN concentrate in a MCT diluent. The mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity.

Example 12

| Contents | Quantity [g] |
| --- | --- |
| GTN (5%) in diluent MCT | 40.1 |
| Myristyl lactate | 20.0 |
| Anhydrous dibasic calcium phosphate | 50.0 |
| Isomalt | 879.9 |
| Peppermint flavoring agent | 10.1 |
| Total | 1000.1 |
| GTN concentration | 0.2% |

Myristyl lactate was mixed with a GTN concentrate in MCT diluent. The mixture was blended well with the anhydrous dibasic calcium phosphate. Then isomalt was added in portions followed by the peppermint flavoring agent and mixing was continued. 200-mg portions of the free-flowing powder were filled in stick packs and stored at 50° C. and at 40° C./75% rel. humidity.

Example 13

| Contents | Quantity [g] |
| --- | --- |
| GTN (5%) in diluent propylene glycol | 4.0 |
| Glycerol monocaprylocaprate Ph. Eur. | 1.0 |
| Anhydrous dibasic calcium phosphate | 5.0 |
| Isomalt | 89.0 |
| Peppermint flavoring agent | 1.0 |
| Total | 100.00 |
| GTN concentration | 0.2% |

GTN concentrate in propylene glycol diluent was blended well with the anhydrous dibasic calcium phosphate. In a separate vessel the glycerol monocaprylocaprate was melted at 40° C. and added to the absorbed diluted GTN. Then isomalt was added in portions followed by the peppermint flavoring agent and mixing was continued. 200-mg portions of the free-flowing powder were filled in stick packs and stored at 50° C. and at 40° C./75% rel. humidity.

Example 14

| Contents | Quantity [g] |
| --- | --- |
| GTN (5%) in diluent propylene glycol | 4.0 |
| Oleoyl macrogol-6-glycerides | 2.0 |
| Anhydrous dibasic calcium phosphate | 5.0 |
| Isomalt | 88.0 |
| Peppermint flavoring agent | 1.0 |
| Total | 100.0 |
| GTN concentration | 0.2% |

GTN concentrate in propylene glycol diluent was blended well with the anhydrous dibasic calcium phosphate, oleoyl macrogol-6-glycerides were added to the absorbed diluted GTN. Then isomalt was added in portions followed by the peppermint flavoring agent and mixing was continued. 200-mg portions of the free-flowing powder were filled in stick packs and stored at 50° C. and at 40° C./75% rel. humidity.

It is expected that the GTN-containing formulations of Examples 10-14 will again demonstrate the advantages of the inclusion of a stabilizer in the above-described GTN absorbate compositions even when held at stressful storage temperatures such as 50° C.

As described elsewhere herein, the preparations exemplified above according to the invention can be supplied as a single dose in the form of a stick pack, a capsule or a sachet. In addition, it is possible to manufacture tablets, mini-tablets or pellets for oromucosal or sublingual administration from the stabilized powders or granules, as necessary, following the addition of other fillers, disintegrants, glidants, binders, and lubricants using routine and customary protocols.

The invention claimed is:

1. A solid pharmaceutical preparation comprising a homogenous admixture comprising phlegmatized glyceryl trinitrate (GTN) and at least one non-volatile polyethoxylated glyceride having a melting point not higher than 60° C., the homogenous admixture absorbed to a porous, pharmaceutically suitable carrier.

2. The pharmaceutical preparation of claim 1, wherein the GTN content is 0.05-2% by weight of the composition.

3. The pharmaceutical preparation of claim 1, wherein the GTN content is 0.1-1% by weight of the composition.

4. The pharmaceutical preparation of claim 1, wherein the GTN content is 0.2% by weight of the composition.

5. The pharmaceutical preparation of claim 1, wherein the GTN content is 0.15% by weight of the composition.

6. The pharmaceutical preparation of claim 1, wherein the GTN content is 0.1% by weight of the composition.

7. The pharmaceutical preparation of claim 1, wherein the non-volatile polyethoxylated glyceride is solid or semi-solid at a temperature of 20° C.

8. The pharmaceutical preparation of claim 1, wherein the polyethoxylated glyceride content is 0.2-10% by weight of the composition.

9. The pharmaceutical preparation of claim 1, wherein the polyethoxylated glyceride is oleoyl macrogol-glyceride.

10. The pharmaceutical preparation of claim 9, wherein the oleoyl macrogol-glyceride content is 2% by weight of the composition.

11. The pharmaceutical preparation of claim 1, wherein the mass ratio of the non-volatile polyethoxylated glycerides to GTN is between 2 and 40.

12. The pharmaceutical preparation of claim 1, wherein the mass ratio of diluent to the non-volatile polyethoxylated glycerides is between 1 and 9.5.

13. The pharmaceutical preparation of claim 1, wherein the carrier is selected from the group consisting of: dibasic calcium phosphate, magnesium aluminometasilicate, and isomalt.

14. The pharmaceutical preparation of claim 1, wherein the carrier is dibasic calcium phosphate.

15. The pharmaceutical preparation of claim 1 further comprising an excipient suitable for sublingual administration, wherein the excipient is selected from the group consisting of: water-soluble mono-, di-, and polysaccharides, as well as their respective alcohols.

16. The pharmaceutical preparation of claim 15, wherein the excipient is selected from the group consisting of: fructose, glucose, isomalt, lactose, maltose, maltitol, mannitol, sorbitol, sucrose, trehalose, and xylitol and mixtures thereof.

17. The pharmaceutical preparation of claim 16, wherein the excipient is isomalt.

18. The pharmaceutical preparation of claim 17, wherein the isomalt content is 70-95% by weight of the composition.

19. The pharmaceutical preparation of claim 17, wheren the composition further comprises xylitol as a second excipient, and wherein isomalt and xylitol combined are 20-95% by weight of the composition.

20. The pharmaceutical preparation of claim 1, wherein the preparation is in the form of a free-flowing powder or free-flowing granules.

21. The pharmaceutical preparation of claim 20, wherein the preparation is packaged as a single dose in the form of a stick pack or sachet.

22. The pharmaceutical preparation of claim 1, wherein the preparation further comprises at least 0.01-3.0% by weight of a flavoring agent.

23. The pharmaceutical preparation of claim 22, wherein the flavoring agent is peppermint.

24. A method of making the pharmaceutical preparation of claim 16, the method comprising the steps of:
    admixing the phlegmatized GTN with the at least one non-volatile polyethoxylated glyceride;
    absorbing the admixture to the porous, pharmaceutically suitable carrier to form an absorbate; and
    mixing the absorbate with the excipient.

25. The method of claim 24, wherein the at least one non-volatile polyethoxylated glyceride is oleoyl macrogol-glyceride.

26. The method of claim 24, wherein the excipient is isomalt.

27. A solid pharmaceutical preparation for oromucosal or oral administration comprising:
    0.05-2% by weight phlegmatized glyceryl trinitrate (GTN);
    dibasic calcium phosphate;
    isomalt as an excipient; and
    at least one non-volatile polyethoxylated glyceride having a melting point not higher than 60° C.,
    wherein the solid pharmaceutical preparation is a homogeneous, free-flowing absorbate.

28. A solid pharmaceutical preparation consisting essentially of:
    a homogenous admixture comprising phlegmatized glyceryl trinitrate (GTN) and at least one non-volatile polyethoxylated glyceride having a melting point not higher than 60° C., the homogenous admixture absorbed to a porous, pharmaceutically suitable carrier;
    an excipient; and
    a flavouring agent,
    wherein the GTN content is 0.05-2% by weight of the composition,
    wherein the polyethoxylated glyceride content is 0.2-10% by weight of the composition,
    wherein the excipient content is 70-95% by weight of the composition, and
    wherein the flavoring agent content is 0.01-3.0% by weight of the composition.

29. A solid pharmaceutical preparation for oromucosal or oral administration comprising:
    0.05-2% by weight phlegmatized glyceryl trinitrate (GTN);
    dibasic calcium phosphate;
    isomalt as an excipient; and
    oleoyl macrogol-glyceride,
    wherein the solid pharmaceutical preparation is a homogeneous, free-flowing absorbate.

* * * * *